(12) United States Patent
Boutros

(10) Patent No.: US 10,463,912 B2
(45) Date of Patent: Nov. 5, 2019

(54) BI-DIRECTIONAL OXYGENATION APPARATUS FOR A NON-INTUBATED PATIENT

(71) Applicant: Sean Boutros, Houston, TX (US)

(72) Inventor: Sean Boutros, Houston, TX (US)

( * ) Notice: Subject to any disclaimer, the term of this patent is extended or adjusted under 35 U.S.C. 154(b) by 0 days.

(21) Appl. No.: 16/367,887

(22) Filed: Mar. 28, 2019

(65) Prior Publication Data
US 2019/0217155 A1 Jul. 18, 2019

Related U.S. Application Data

(63) Continuation-in-part of application No. 15/837,532, filed on Dec. 11, 2017, now Pat. No. 10,252,021, which is a continuation-in-part of application No. 15/672,530, filed on Aug. 9, 2017, now Pat. No. 10,080,511.

(51) Int. Cl.
| | |
|---|---|
| *A63B 23/18* | (2006.01) |
| *A61M 16/04* | (2006.01) |
| *A61M 16/20* | (2006.01) |

(52) U.S. Cl.
CPC ........... *A63B 23/18* (2013.01); *A61M 16/049* (2014.02); *A61M 16/208* (2013.01); *A61M 2205/0216* (2013.01)

(58) Field of Classification Search
CPC .. A61M 16/20; A61M 16/201; A61M 16/204; A61M 16/205; A61M 16/206; A61M 16/207; A61M 16/208; A61M 16/209; A61M 16/049; A61M 15/0016; A61M 16/10; A63B 23/18; A63B 23/00; A63B 23/02; A41D 13/11; A62B 7/00; A62B 7/10; A62B 9/06; B63C 11/18; B63C 11/205; B63C 11/22; B63C 9/00; B63C 9/1255
USPC ............ 128/200.14, 200.24, 201.11, 201.25, 128/201.26, 201.28, 202.14, 202.28, 128/202.29, 203.11, 203.12, 204.26, 128/205.13, 205.24, 205.27, 205.29, 128/206.11, 206.12, 206.15, 206.17, 128/207.12, 207.13, 207.14, 207.16, 128/207.18, 207.29, 848, 859, 861, 863
See application file for complete search history.

*Primary Examiner* — Jan Christopher L Merene
*Assistant Examiner* — Elliot S Ruddie
(74) *Attorney, Agent, or Firm* — Dale J. Ream

(57) ABSTRACT

A self-administered oxygenation apparatus for increasing pressure within a non-intubated patient's lungs and thereby increasing an amount of oxygen in the non-intubated patient's blood when operated by the patient includes a mouthpiece, a vent member, and a resistance member. The mouthpiece includes an external portion defining a center orifice through which the patient selectively inhales and exhales air. The resistance member is a PEEP valve positioned between the interior area of the vent member and the mouthpiece, the resistance member having a flexible construction configured to open upon inhalation so as to allow ambient air inhaled by the patient to pass thereby without resistance and to close upon exhalation, exhalation causing an end shield to pivot outwardly from the vent member under a bias of external elastic members.

19 Claims, 23 Drawing Sheets

BI-DIRECTIONAL OXYGENATION APPARATUS FOR A NON-INTUBATED PATIENT

REFERENCE TO RELATED APPLICATIONS

This application claims the benefit of non-provisional patent application Ser. No. 15/837,532 filed Dec. 11, 2017 titled Bi-Directional Oxygenation Apparatus for a Non-Intubated Patient, which claims the benefit of U.S. Ser. No. 15/672,530 filed Aug. 9, 2017 titled Bi-Directional Oxygenation Apparatus for a Non-Intubated Patient (now U.S. Pat. No. 10,080,511) both of which are incorporated in their entirety herein by reference.

BACKGROUND OF THE INVENTION

This invention relates generally to medical equipment intended to increase oxygenation of the blood of a patient who has insufficient pressure in the lungs following exhalation.

Patients in respiratory distress are often hospitalized and, sometimes, require invasive treatment such as intubation and being connected to a machine that both inhales and exhales for them. An electrical breathing machine may be incorporated to generate the mechanics of breathing. The patient in such cases may be unable to inhale or exhale on his own, or at least efficiently. In such instances, doctors may desire respiratory treatments intended to increase the oxygenation of the patient's blood by increasing pressure in the patient's airway.

However, there are patients and even athletes that have non-critical respiratory ailments or conditions that could benefit from increasing the pressure within their airway and, as a result, increasing the oxygenation of their blood. Such individuals are not intubated and do not require a breathing machine to either inhale ambient air or exhale air from their lungs. Putting positive pressure on the lungs of an otherwise unassisted breathing patient or user, such as by resisting normal exhalation, would enhance the oxygenation of the patient's blood and improve his breathing capacity or efficiency.

Although presumably effective for its intended use, the current method of treating a dangerously distressed patient with a full ventilator and intubated patient is undesirable for a patient that is not intubated and not being treated on a full ventilator setup. Stated another way, it would be desirable for a patient capable of inhaling and exhaling on his own to have a bi-directional oxygenation apparatus that allows the patient to inhale air through his mouth and then to exhale through his mouth with mechanical resistance being given to the exhalation, whereby to increase the pressure on the airway, expand any collapsed alveoli in the lungs and, as a result, increase oxygenation of the blood. In addition, it would be desirable to have a bi-directional oxygenation apparatus having a mouthpiece.

SUMMARY OF THE INVENTION

A self-administered oxygenation apparatus according to the present invention for increasing pressure within a non-intubated patient's lungs and thereby increasing an amount of oxygen in the non-intubated patient's blood when operated by the patient includes a mouthpiece, a vent member, and a resistance member. The mouthpiece includes an external portion defining a center orifice through which the patient selectively inhales and exhales air. The vent member includes a continuous side wall fixedly coupled to the external portion of the mouthpiece and defining an interior area in fluid communication with the center orifice. The resistance member is positioned between the interior area of the vent member and the mouthpiece, the resistance member having a single panel construction coupled to a wall of the vent member and operable to move pivotally between an open configuration upon inhalation so as to allow ambient air inhaled by the patient to pass thereby without resistance and a closed configuration blocking a portion of exhaled air for decreasing the airflow of exhalation and thereby increasing the pressure inside the airway.

Therefore, a general object of this invention is to provide a bi-directional oxygenation apparatus for a patient that includes a mouthpiece that enables the patient to both inhale and exhale air through his mouth.

Another object of this invention is to provide a bi-directional oxygenation apparatus, as aforesaid, that includes a resistance portion that provides resistance to exhaled air so as to expand the patient's airway and increase oxygenation of the patient's blood.

Still another object of this invention is to provide a bi-directional oxygenation apparatus, as aforesaid, in which inhaled air is allowed to pass without resistance as the resistance member is normally biased to an open position.

Yet another object of this invention is to provide a bi-directional oxygenation apparatus, as aforesaid, in which the resistance member is moved to bear against an end shield and configured to decrease a flow of air that is passing outwardly therethrough during exhalation.

A further object of this invention is to provide a bi-directional oxygenation apparatus, as aforesaid, having at least one external elastic member that may be configured to bias an end shield in a closed configuration.

A still further object of this invention is to provide a bi-directional oxygenation apparatus, as aforesaid, in which mechanical resistance to exhaled air expands any collapsed alveoli in the patient's lungs.

Other objects and advantages of the present invention will become apparent from the following description taken in connection with the accompanying drawings, wherein is set forth by way of illustration and example, embodiments of this invention.

DESCRIPTION OF THE PREFERRED EMBODIMENT

Figure 1:
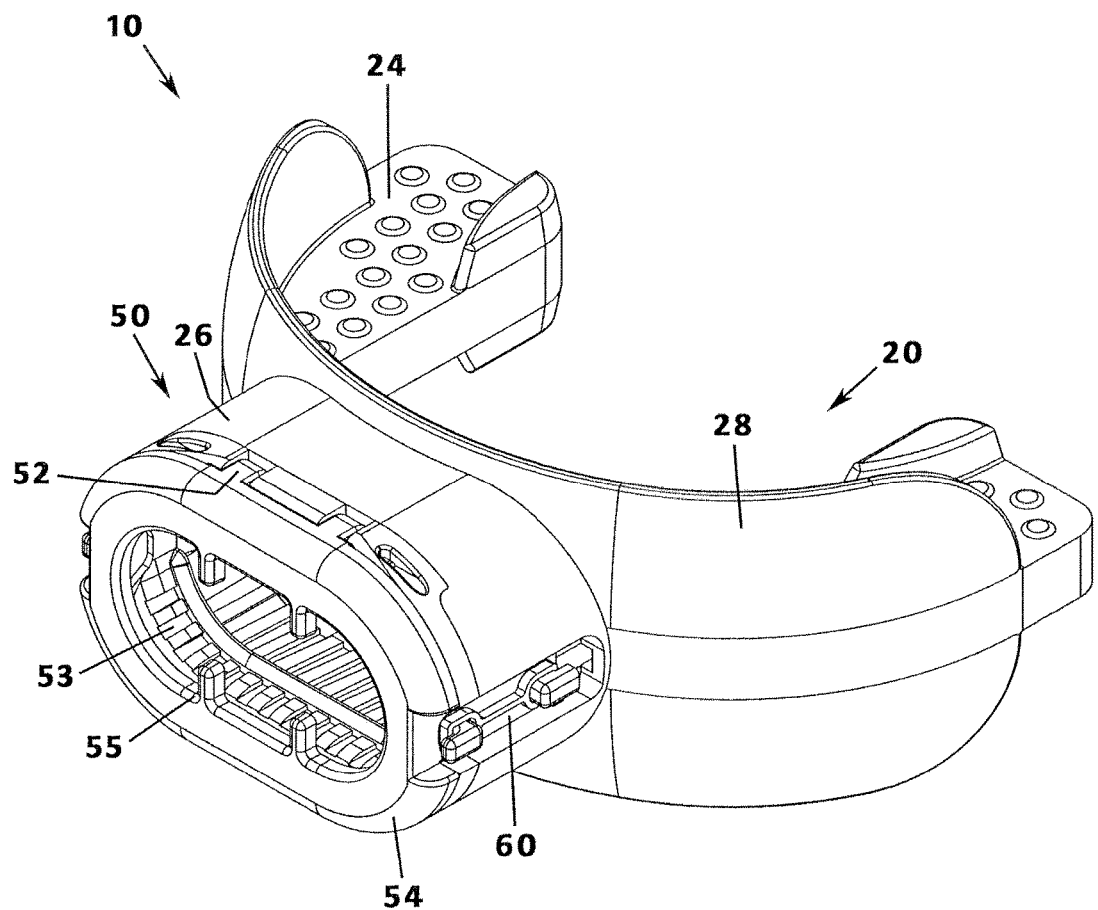
FIG. 1 is a front perspective view of a bi-directional oxygenation apparatus according to an embodiment of the present invention.
Figure 2:
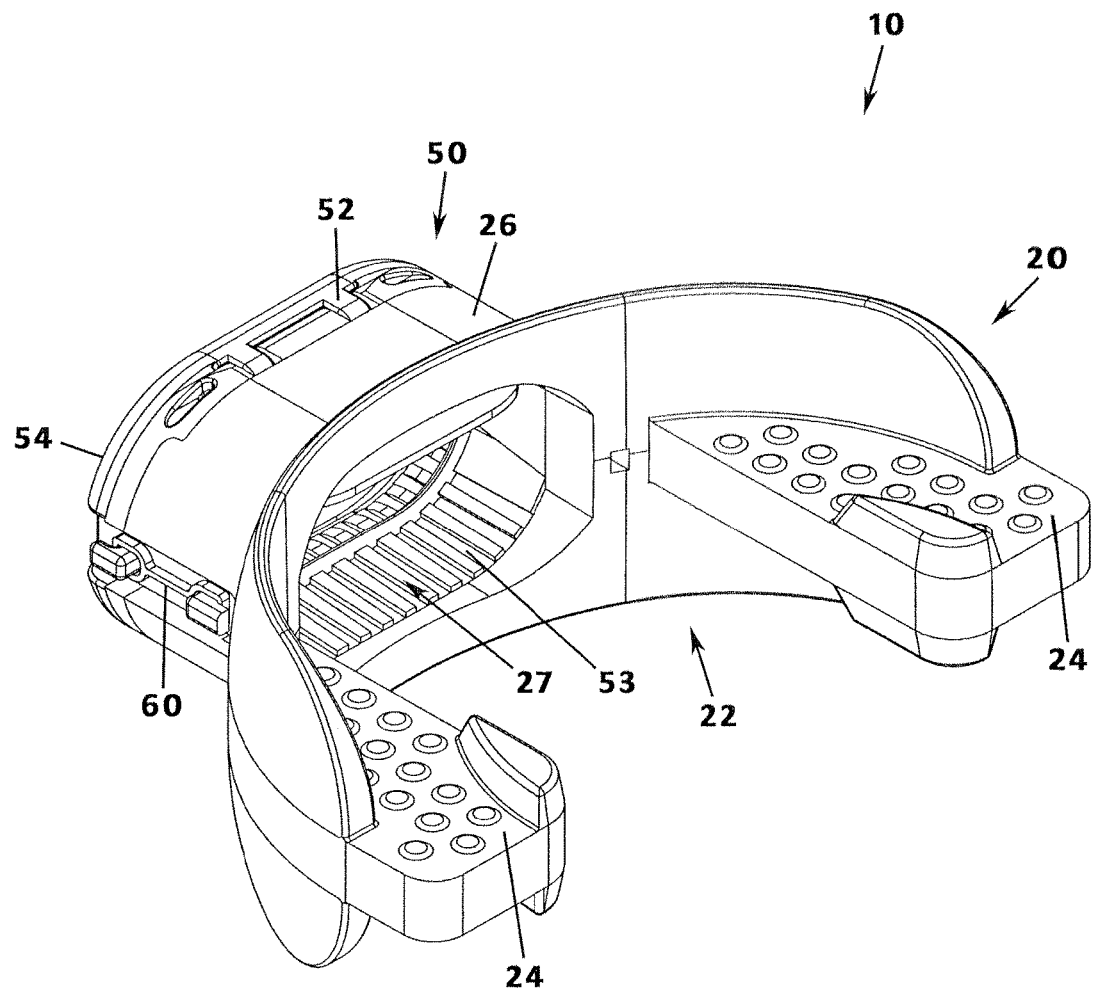
FIG. 2 is a rear perspective view of the of the bi-directional oxygenation apparatus as in FIG. 1.
Figure 3:
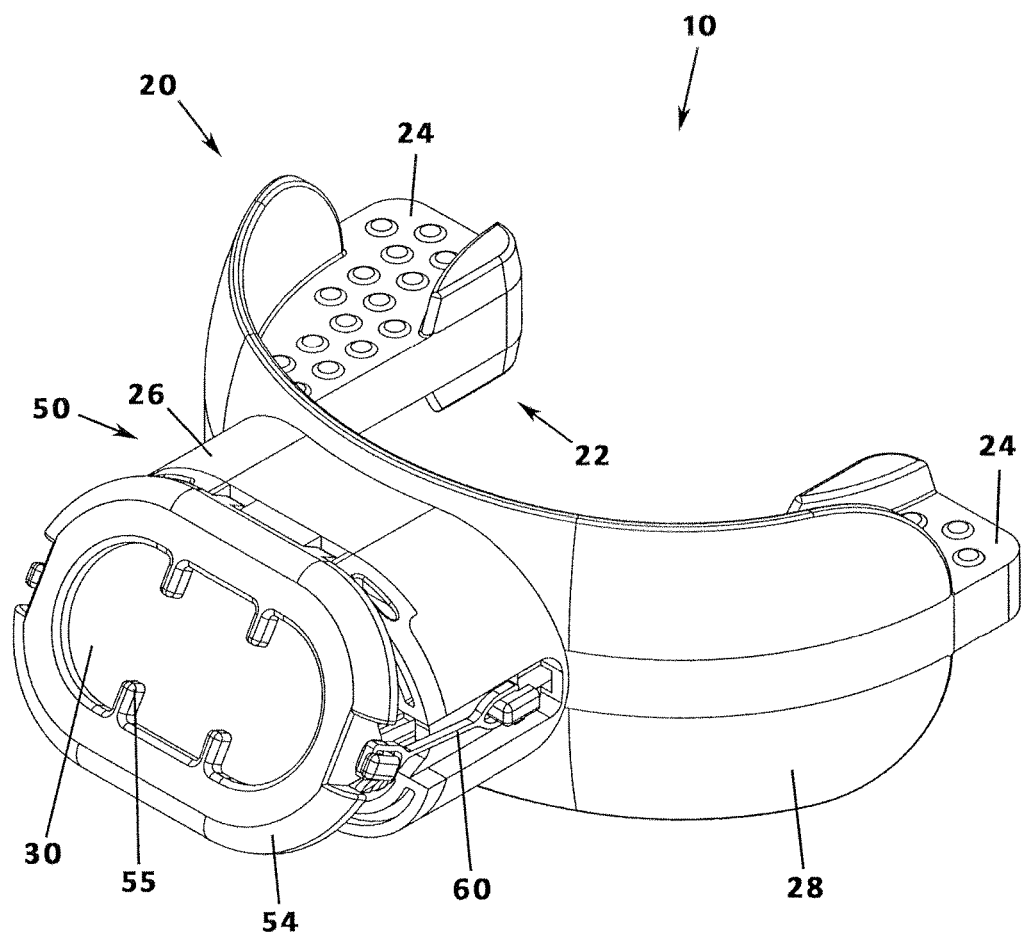
FIG. 3 is a front perspective view of the bi-directional oxygenation apparatus shown with the end shield in an extended configuration.
Figure 4:
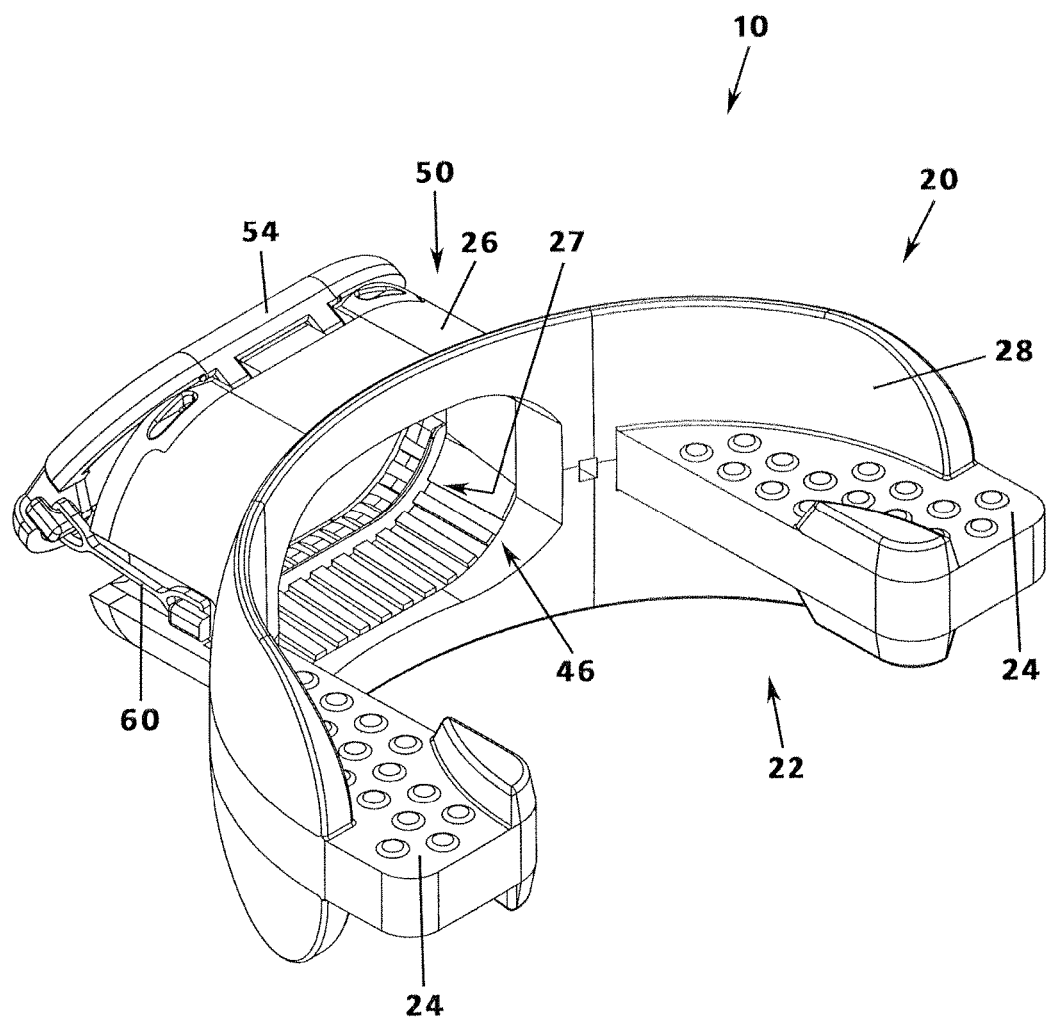
FIG. 4 is a rear perspective view of the bi-directional oxygenation apparatus as in FIG. 3.
Figure 5:
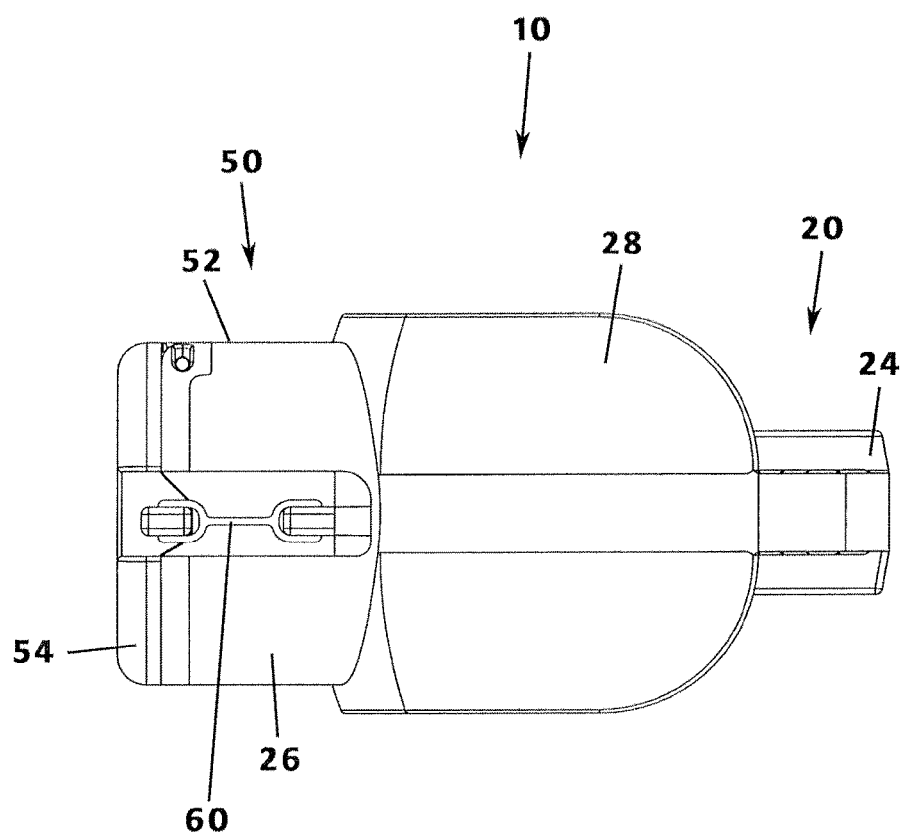
FIG. 5 is a side view of the bi-directional oxygenation apparatus as in FIG. 1.
Figure 6:
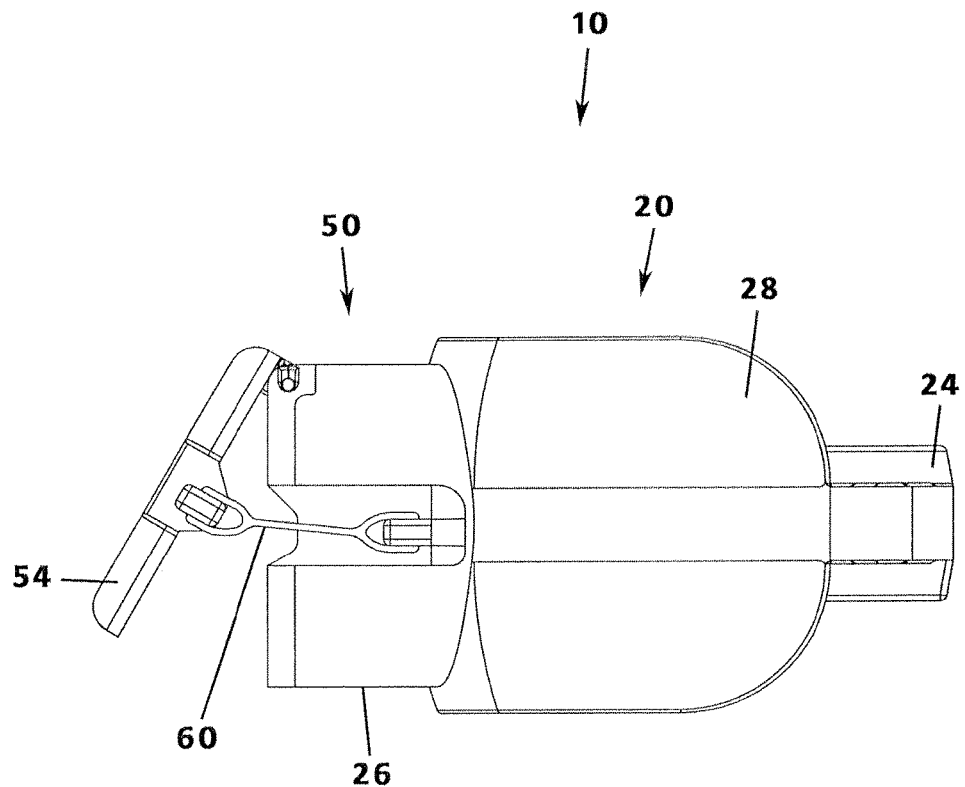
FIG. 6 is a side view of the bi-directional oxygenation apparatus as in FIG. 3.
Figure 7:
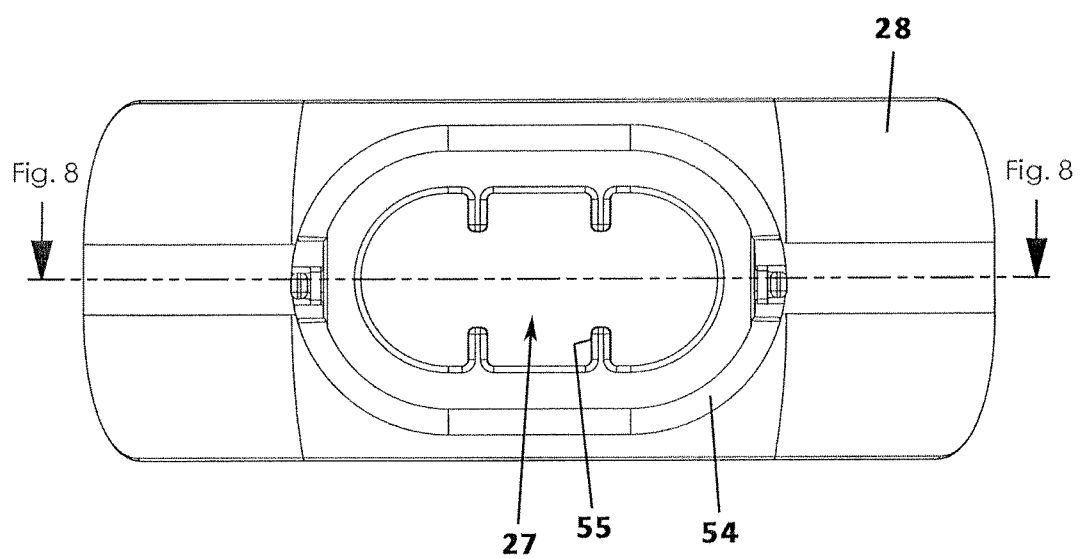
FIG. 7 is a front view of the bi-directional oxygenation apparatus as in FIG. 1.
Figure 8:
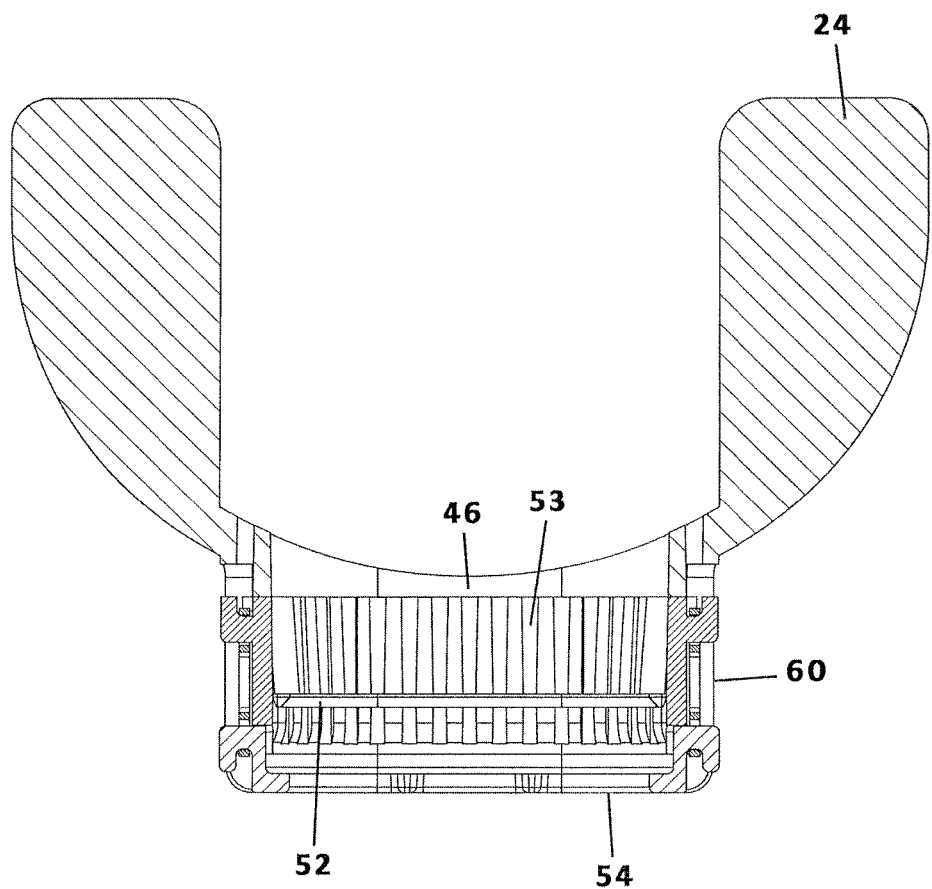
FIG. 8 is a sectional view taken along line 8-8 of FIG. 7.
Figure 9:
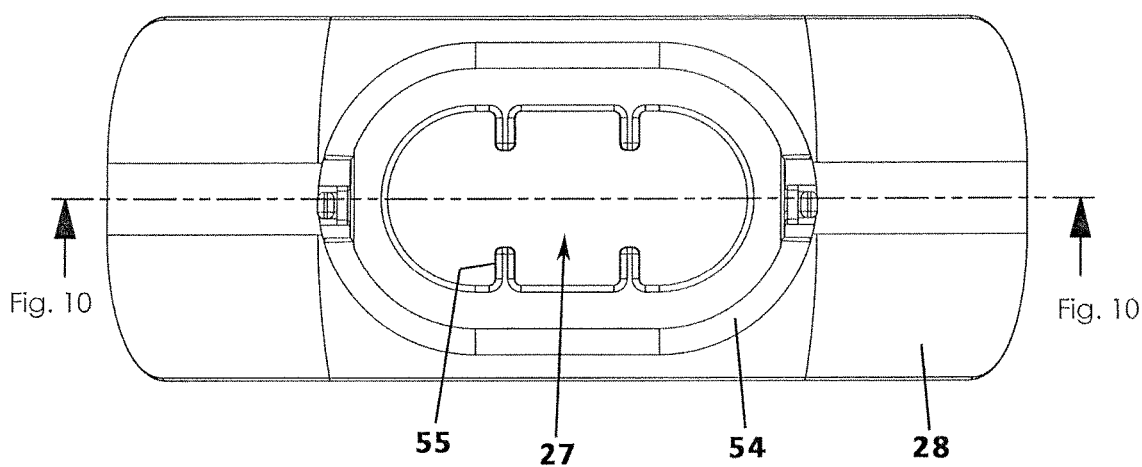
FIG. 9 is a front view of the bi-directional oxygenation apparatus as in FIG. 1.
Figure 10:
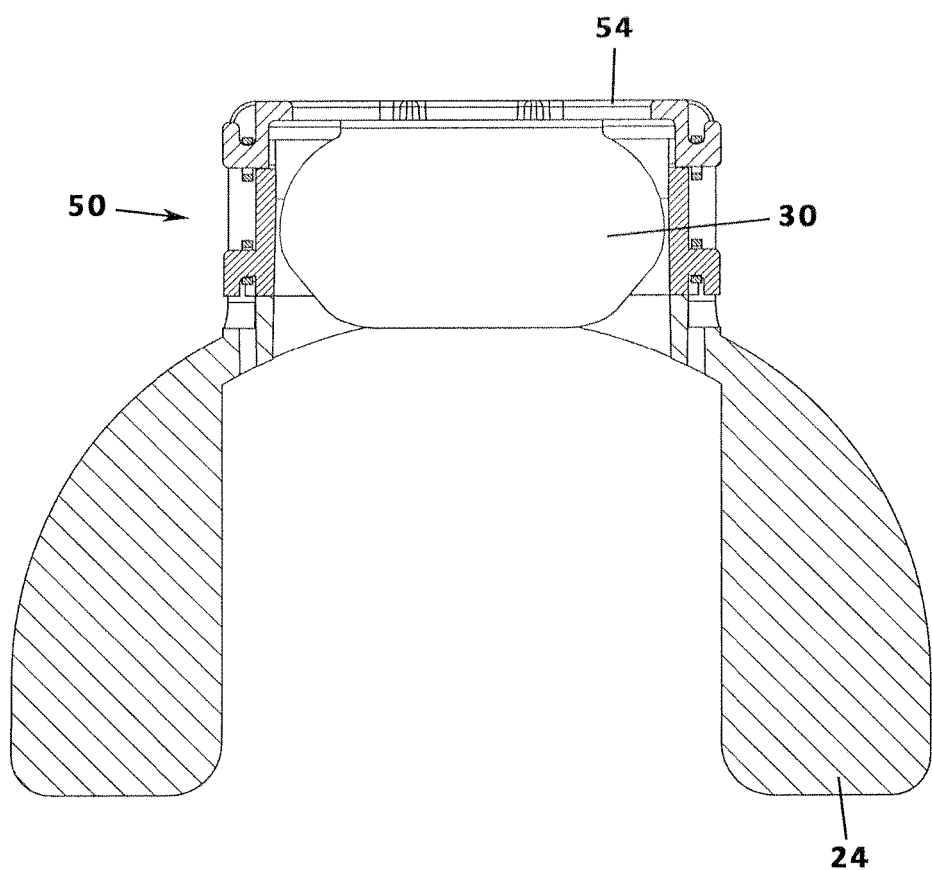
FIG. 10 is a sectional view taken along line 10-10 of FIG. 9.
Figure 11:
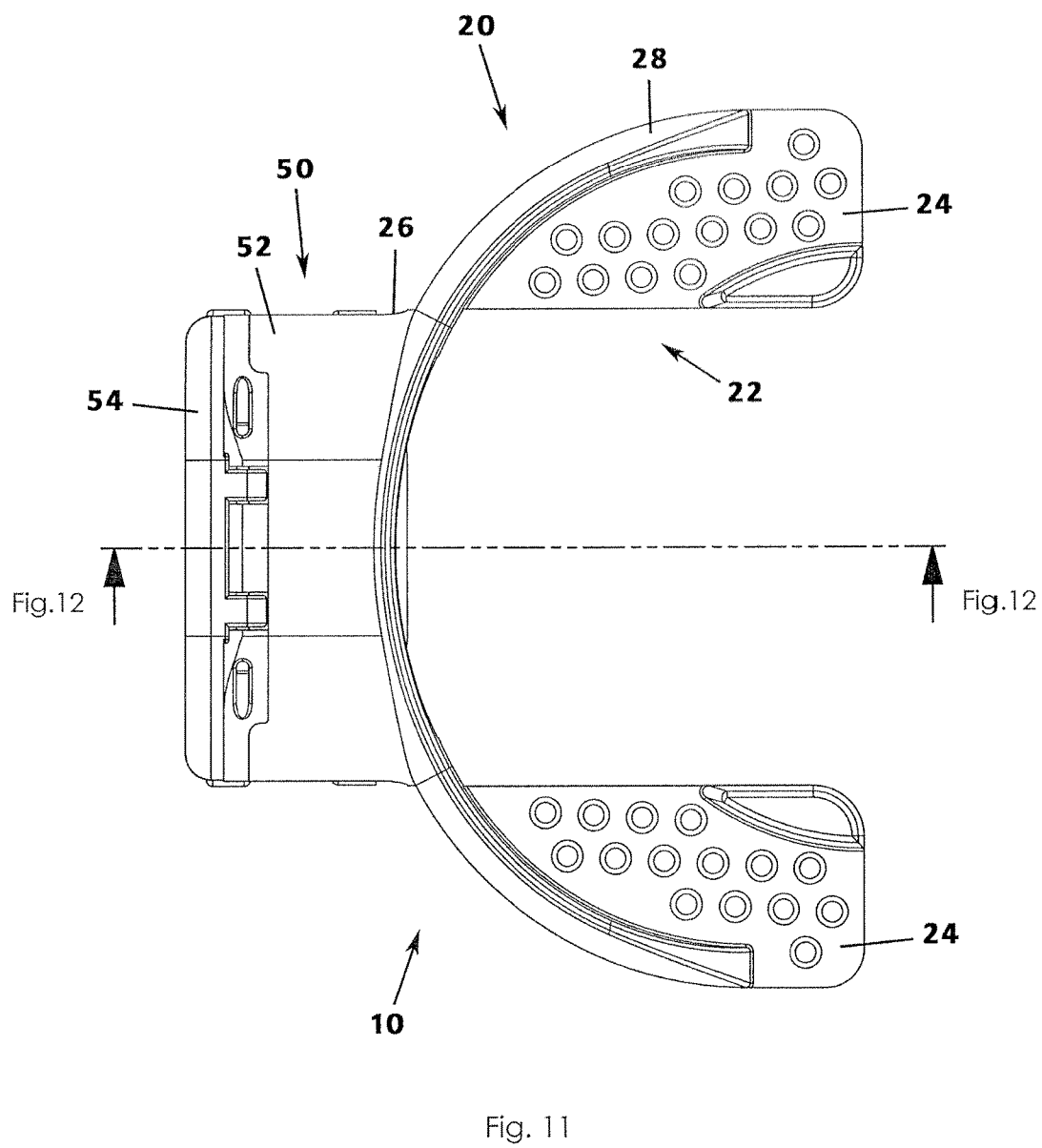
FIG. 11 is a top view of the bi-directional oxygenation apparatus as in FIG. 1.
Figure 12:
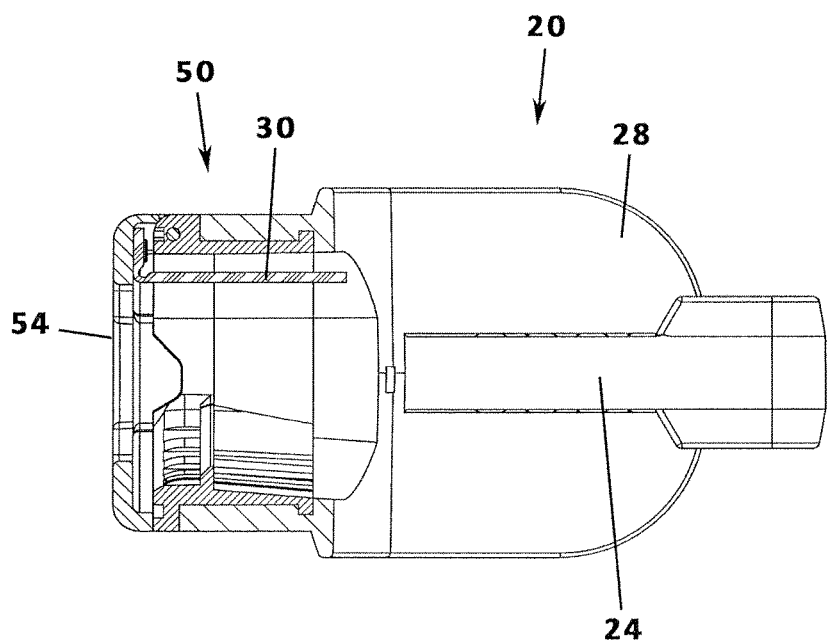
FIG. 12 is a sectional view taken along line 12-12 of FIG. 11.
Figure 13:
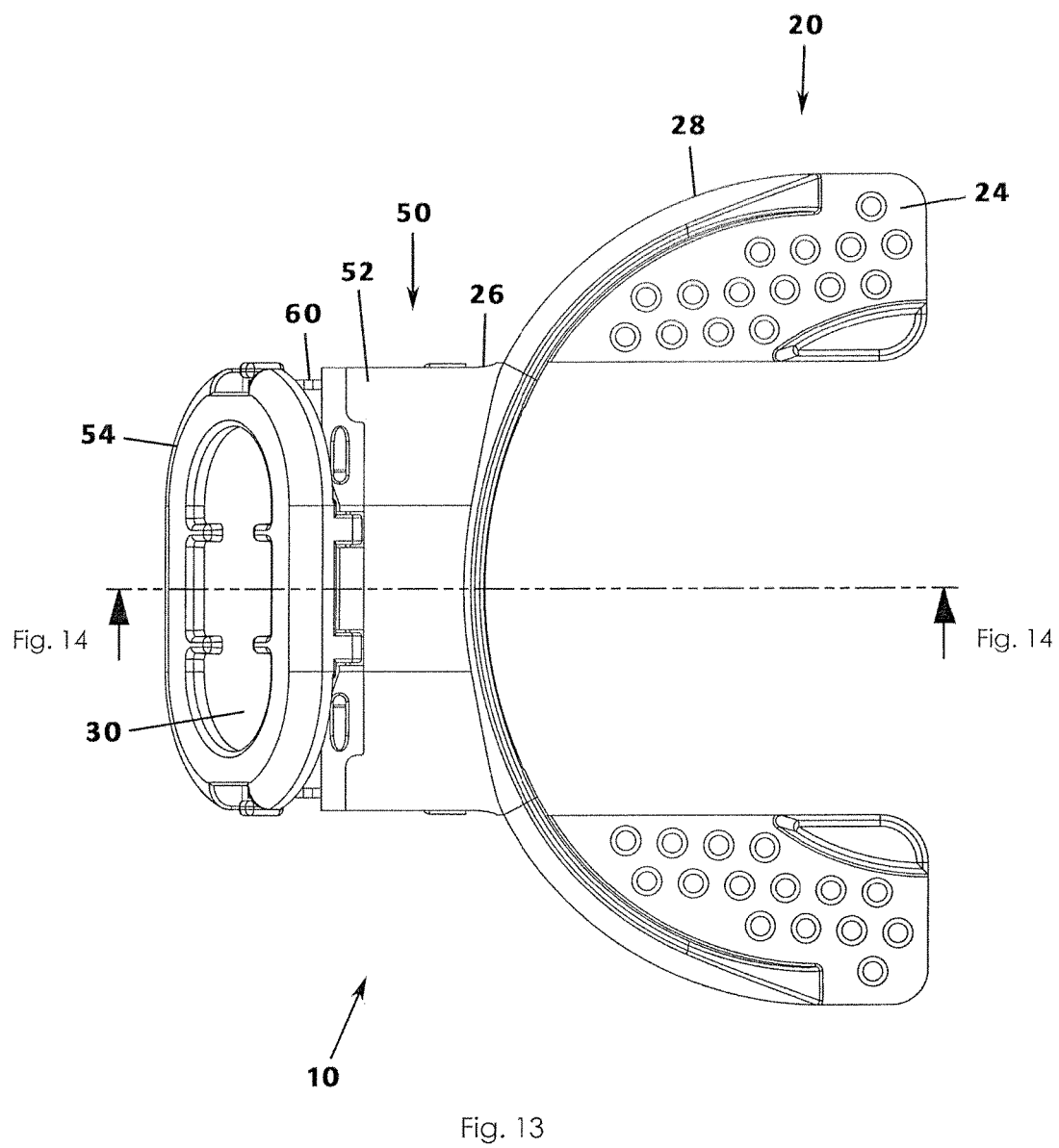
FIG. 13 is a top view of the bi-directional oxygenation apparatus as in FIG. 3.
Figure 14:
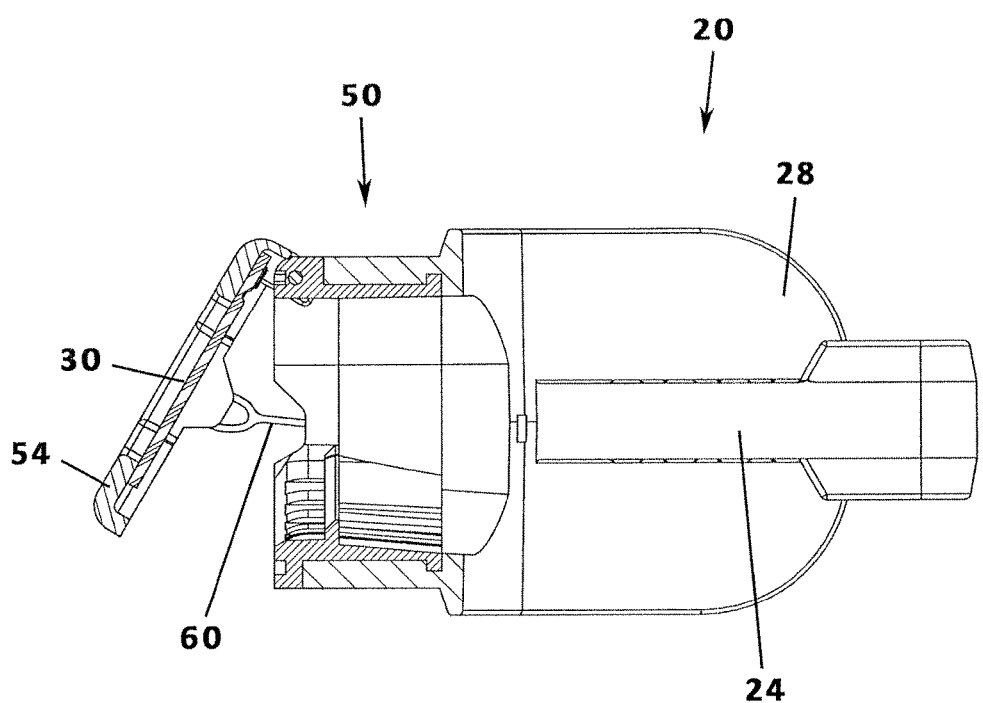
FIG. 14 is a sectional view taken along line 14-14 of FIG. 12.
Figure 15:
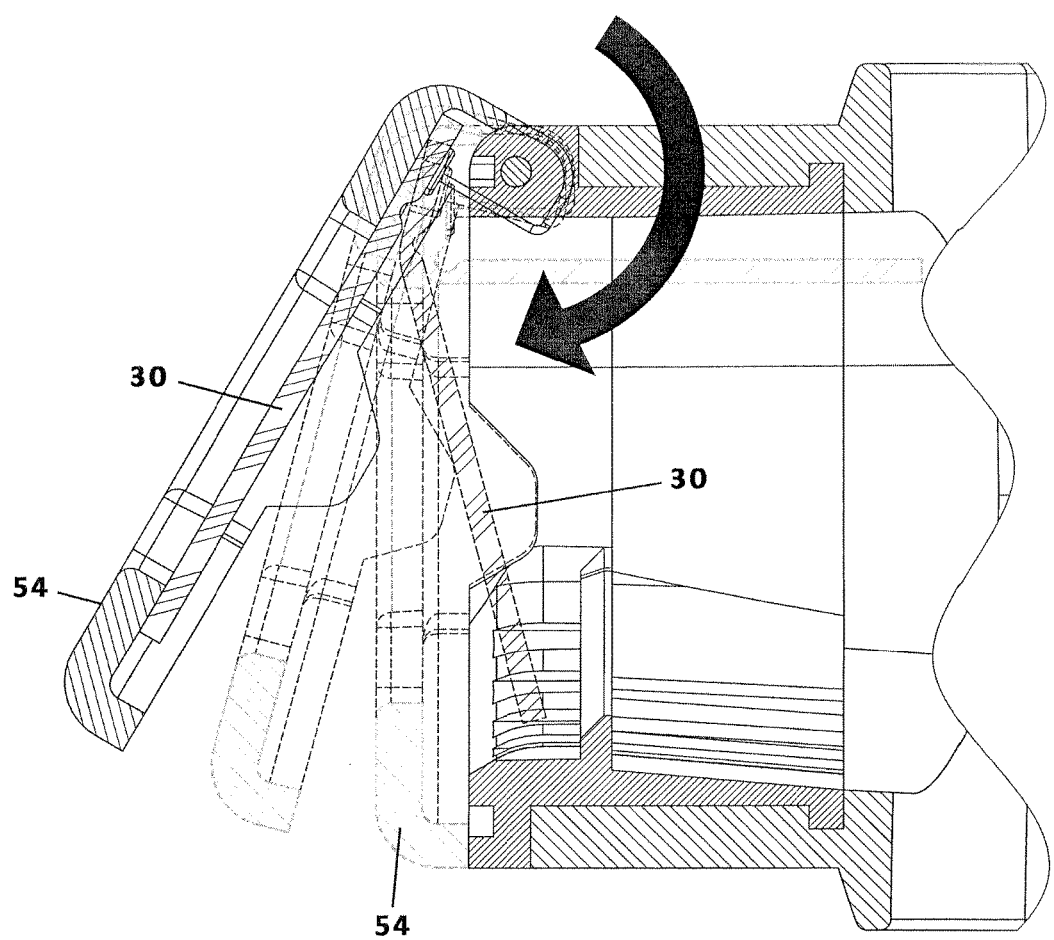
FIG. 15 is a side view of a portion of FIG. 3 showing the pivotal movements of the end shield according to the present invention.

A bi-directional oxygenation apparatus for a patient according to a preferred embodiment will now be described with reference to FIGS. 1 to 23 of the accompanying drawings. The bi-directional oxygenation apparatus 10 includes a mouthpiece 20 having an external portion 26, a resistance member 30 for regulating inhalation and exhalation resistance, and a vent member 50. As will be described in greater detail later, the vent member 50 may also be referred to as a vent port through which ambient air is inhaled into the device and inhaled air is exhaled. It will be understood that references to a "patient" herein also contemplates users not under the care of any doctor and, therefore, not a typical 'patient," such as an athlete using the oxygenation apparatus 10 while practicing or while engaged in game play.

It is understood that references herein to a patient refer to a patient who is not intubated or being treated on a complete respiratory system that essentially inhales and exhales for the patient. Rather, the present invention is for use by a non-intubated patient who is able to inhale and exhale on his own while yet being in need of improved and increased oxygenation of his blood. For instance, an athlete or rehabilitation patient may use the present invention to utilize his own inhalation and exhalation of air to expand his lungs and increase oxygenation of his blood. The present invention, in fact, may include an external mouth shield 40 for protecting the oxygenation apparatus 10 from damage from impact forces that may be experienced during use as will be described in greater detail later. The external mouth shield 40 is not shown in FIGS. 1-18 for the sake of clarity of elements that would be hidden thereby but is shown in figures thereafter and is a component of the present invention.

The bi-directional oxygenation apparatus 10 includes a mouthpiece 20 that includes an intraoral portion 22 configured for placement inside a patient's mouth and an external portion 26 coupled to the intraoral portion 22 and configured to remain outside the patient's mouth. In its simplest form, the intraoral portion 22 has structures similar to those of a football mouthpiece that may be gripped in between the teeth of a football player. For instance, the mouthpiece 20 may include left and right grip members 24 spaced apart laterally within a horizontal plane or arranged in a bowed configuration complementary to the bowed configuration of a patient's teeth so as to be gripped by the patient's teeth during use (FIG. 1b).

Further, the mouthpiece 20 includes a mouth shield 28 (also referred to as an internal mouth shield) that is positioned intermediate the intraoral portion 22 and the external portion 26. The mouth shield 28 may have a generally hemispherical shape configuration and be both configured and positioned to press against and conform to inner surfaces of the lips and cheeks of the patient when the intraoral portion 22 is taken into the patient's mouth. The external portion 26 of the mouthpiece 20 defines a central orifice 27 through which air may be inhaled and exhaled by a patient as will be described in further detail below. It may be seen that the intraoral portion 22 and external portion 26 define the central orifice 27 in combination or in communication with one another (FIG. 1b).

In an embodiment, the external portion 26 is situated intermediate the vent member 50 and the mouthpiece 20 and provides the structures that make the invention operate efficiently. Specifically, the external portion 26 may have a continuous side wall arranged in an oval shaped configuration although a combination of walls arranged in a rectangular, circular, or irregular configuration would also work. The continuous side wall of the external portion 26 defines a hollow interior space open on both front and rear ends in communication with the central orifice 27 of the mouthpiece 20 and with an open interior area of the vent member 50. In other words, the external portion 26 is essentially a pass through component through which ambient or processed air is inhaled by the patient and through which air from the patient's lungs is exhaled. Preferably, the external portion 26 may have a singular or integrated construction with the mouthpiece 20.

In an embodiment, the vent member 50 may have a unitary construction with the external portion 26 of the mouthpiece 20 such that the vent member 50 is actually connected directly to the mouthpiece 20. Stated another way, the external portion integrally transitions into the vent member 50 and the two elements share the continuous side wall 52 to provide a framework. In another embodiment (not shown), the vent member 50 may have a mounting portion having a diameter slightly smaller than a diameter of the central orifice 27 of the external portion 26 of the mouthpiece 20 so as to be slidably received therein in a tight friction fit arrangement. More particularly, the vent member 50 may include a shape configuration complementary to that of the external portion 26 for coupling in a snap-fit arrangement.

Figure 16:
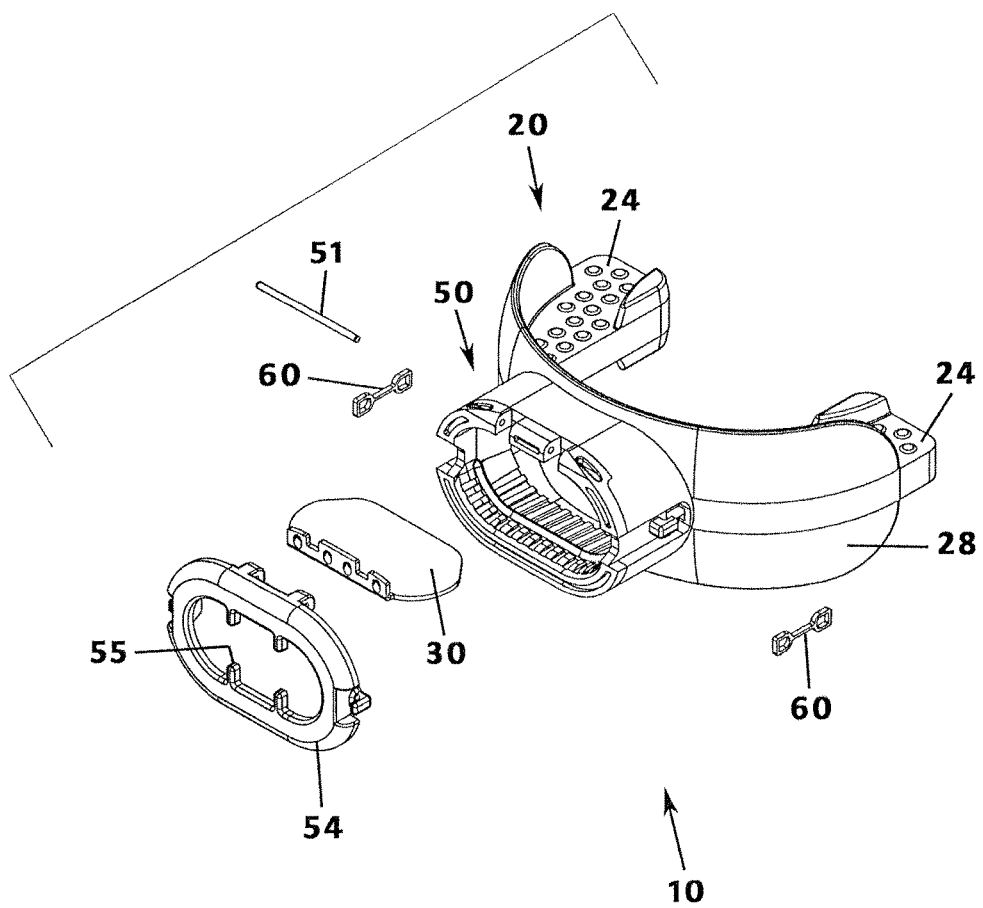
FIG. 16 is an exploded view of the bi-directional oxygenation apparatus as in FIG. 1.
Figure 17:
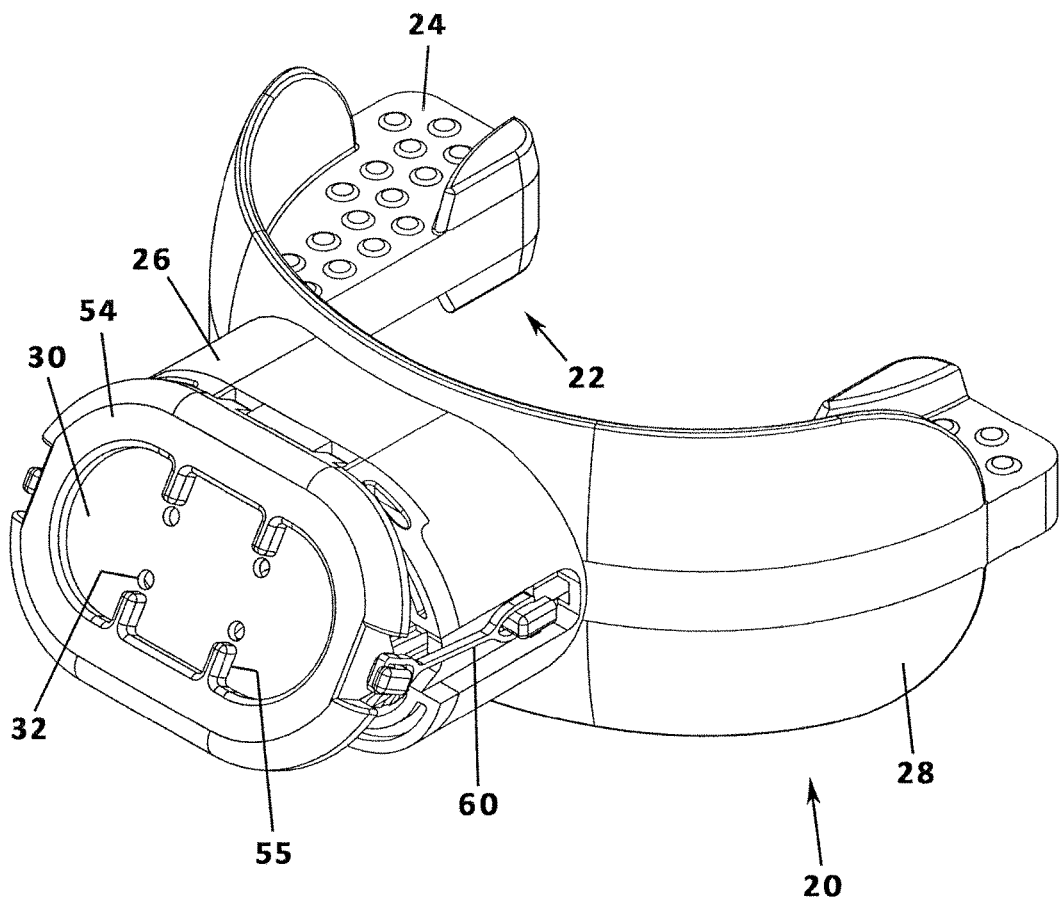
FIG. 17 is a front perspective view of the bi-directional oxygenation apparatus as in FIG. 3, illustrating the aspect of the resistance member having openings.

The vent member 50 is the component through which ambient air is inhaled into the mouthpiece 20 and through which air from a user's lungs is finally exhausted when exhaled. Now more particularly, the vent member 50 includes a continuous side wall 52 that defines an interior area in fluid communication with the central orifice 27 defined by the mouthpiece 20. Preferably, the vent member 50 includes an end shield 54 pivotally coupled to a distal end (i.e. free end) of the continuous side wall 52 and configured to partially block access to the interior space while still allowing inhalation or exhalation of air therethrough. The end shield 54 may be configured as a grill or grate having one or more support members 55. The support members 55 are configured to act as a "stop" or barrier against which the resistance member 30 will bear against when resisting exhaled air. The end shield 54 may include an upper edge pivotally coupled to or in operative contact with a corresponding edge of the distal end of the side wall of the vent member 50, such as with a pin 51 (FIG. 16). The end shield 54 is secured by one or more elastic members 60.

More particularly, the end shield 54 provides resistance against exhalation and may be pushed outwardly away from the end shield 54 according to the resistance of one or more elastic members 60 that bias the end shield 54 toward a closed configuration adjacent the free end of the vent member 50. The elastic member 60 is a loop of resilient material such as rubber. The elastic member 60 may be coupled to respective first and second flanges (unnumbered) in a tightening, biased relationship. For instance a first flange may be mounted on an exterior surface of the vent member 50 and a second flange may be mounted on the end shield 54 with an elastic member 60 extending therebetween. More particularly, the elastic member 60 may be a rubber band having a predetermined amount of tension coupled to respective flanges for normally urging the end shield 54 to bear against the vent member 50, the elastic members 60 biasing the end shield 54 to a closed configuration bearing against the vent member 50. In some embodiments, a gasket or o-ring seal may be sandwiched between the end shield 54 and vent member 50 or other components so as to seal against air leakage in use. In other embodiments (not shown), the elastic member 60 may utilize other types of resistive or tension technology, such as an air piston/cylinder combination that provides a predetermined amount of tension.

Now with further reference to the resistance member 30, the resistance member 30 is mounted inside the interior space defined by the continuous side wall 52 of the vent member 50. The resistance member 30 is positioned intermediate the end shield 54 and the external portion 26 of the mouthpiece 20 so that inhaled and exhaled air must flow past, around, against, or through the resistance member 30, respectively, as will be discussed below. In an embodiment, the resistance member 30 is a single panel, such as a substrate constructed of silicone and having a generally planar configuration and acts as a valve as air is inhaled and exhaled. Preferably, the resistance member 30 is a PEEP valve positioned intermediate the mouthpiece 20 and end shield 54 and is pivotally movable to an open configuration that allows inhaled air to pass without resistance and a closed configuration that imparts a predetermined amount of resistance to air being exhaled from a patient's lung through the directional oxygenation apparatus 10. The PEEP valve 30 may be constructed of silicone and situated to substantially span the open interior space defined by the continuous side wall of the vent member 50.

The resistance member 30 may include an upper edge having structures coupled to complementary structures of an upper surface of the side wall of the vent member 50 and is operably pivotal (such as including a living hinge configuration or being pivotally coupled to the side wall of the vent member). As first described above, the resistance member is pivotally operable to allow ambient air inhaled by the patient to pass thereby without resistance and to decrease a flow of air exhaled by the patient. More specifically, the resistance member is normally positioned at an open configuration and is also moved to an open configuration directed away from the end shield 54 and toward the mouthpiece 20 when air is inhaled for allowing movement of air toward the mouthpiece 20 (so as to be received into the patient's lungs). Conversely, the resistance member 30 may be moved to a closed configuration that bears against the end shield 54 when air is exhaled by the patient for resisting movement of air flowing toward said end shield 54. In fact, movement of the resistance member 30 to the closed configuration may cause the resistance member 30 to push outwardly against the end shield 30, causing the end shield to push the end shield 54 to its extended or opened configuration as shown in FIGS. 3, 4, 6, and 14.

Importantly, the resistance member 30 does not provide an airtight seal at the closed configuration. In other words, even when the resistance member 30 is urged to bear against the end shield 54—even when urging the end shield 54 to open away and be separated from the vent member 50 —the configuration of the resistance member 30 allows a quantity of exhaled air to pass around its peripheral edge and escape or be vented. As a result, a patient can never suffocate even if the pressure of his exhalation is too weak to push open the end shield 54.

Figure 18:
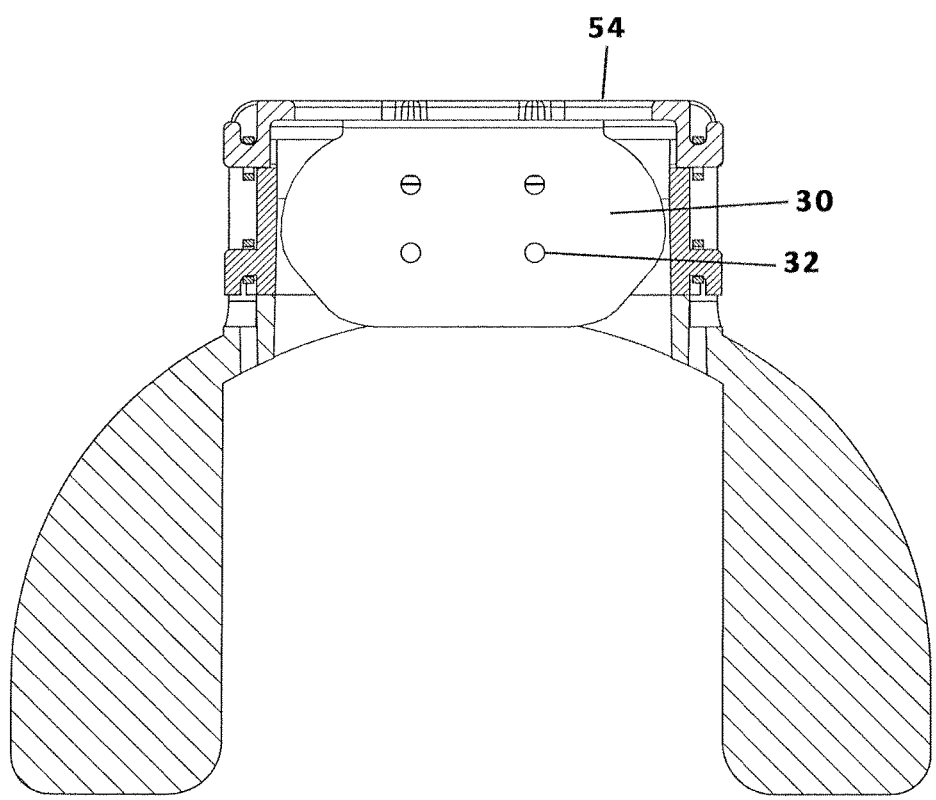
FIG. 18 is a sectional view as in FIG. 10, illustrating the aspect of the resistance member having openings.

The resistance member 30 may have a singular, planar, and flat construction defining no holes or openings through which a predetermined quantity of exhaled air is allowed to pass outside and away from the vent member 50. In another embodiment, the resistance member 30 may define one or more openings 32 spaced apart from one another, such as four holes (FIG. 18). It is understood that the number of holes, the diameter of each hole, or the arrangement of holes may affect the degree of resistance the resistance member may provide to exhaled air bearing against the resistance member 30. In fact, when the resistance member 30 includes holes, the end shield 54 may be fixed and not pivotal.

Figure 19:
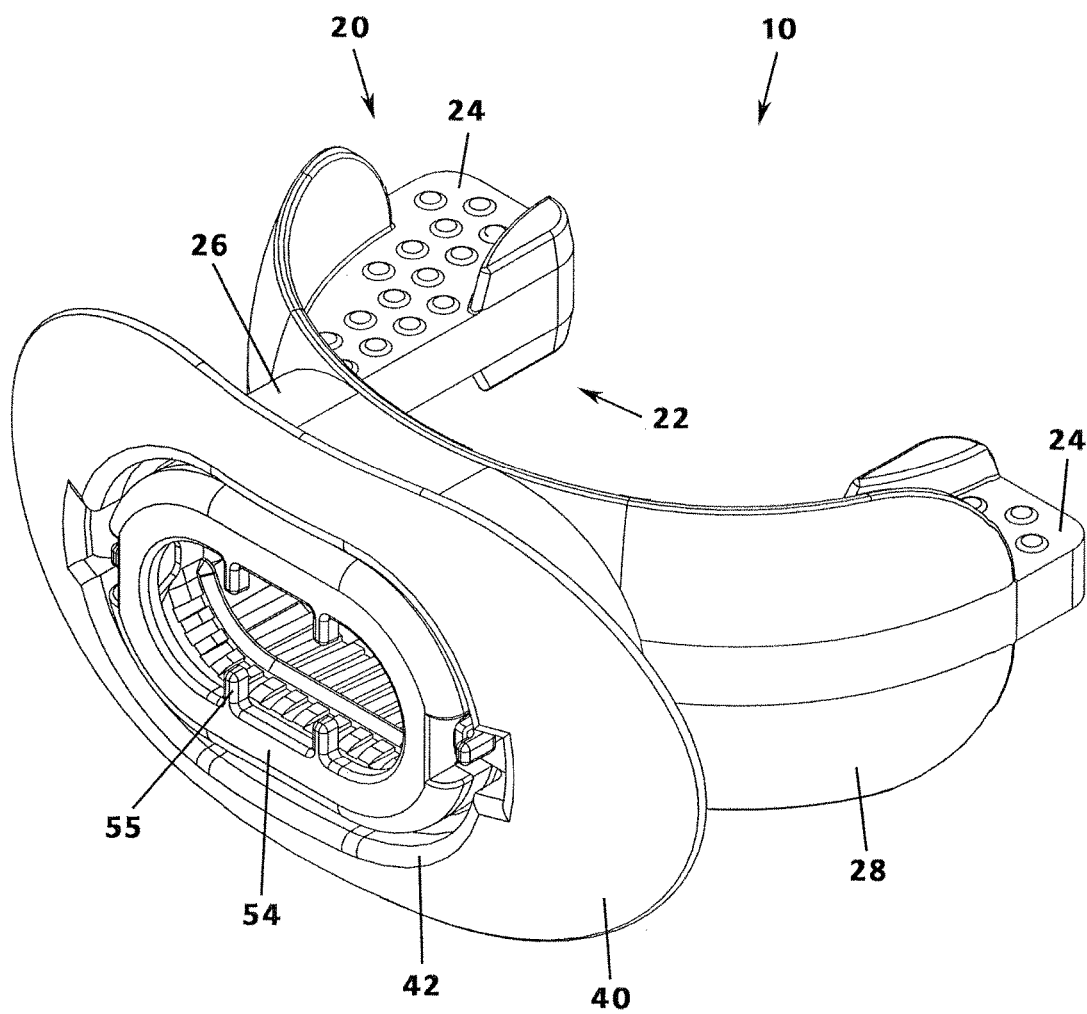
FIG. 19 is a front perspective view of the bi-directional oxygenation apparatus illustrating the external mouth shield of the present invention.
Figure 20:
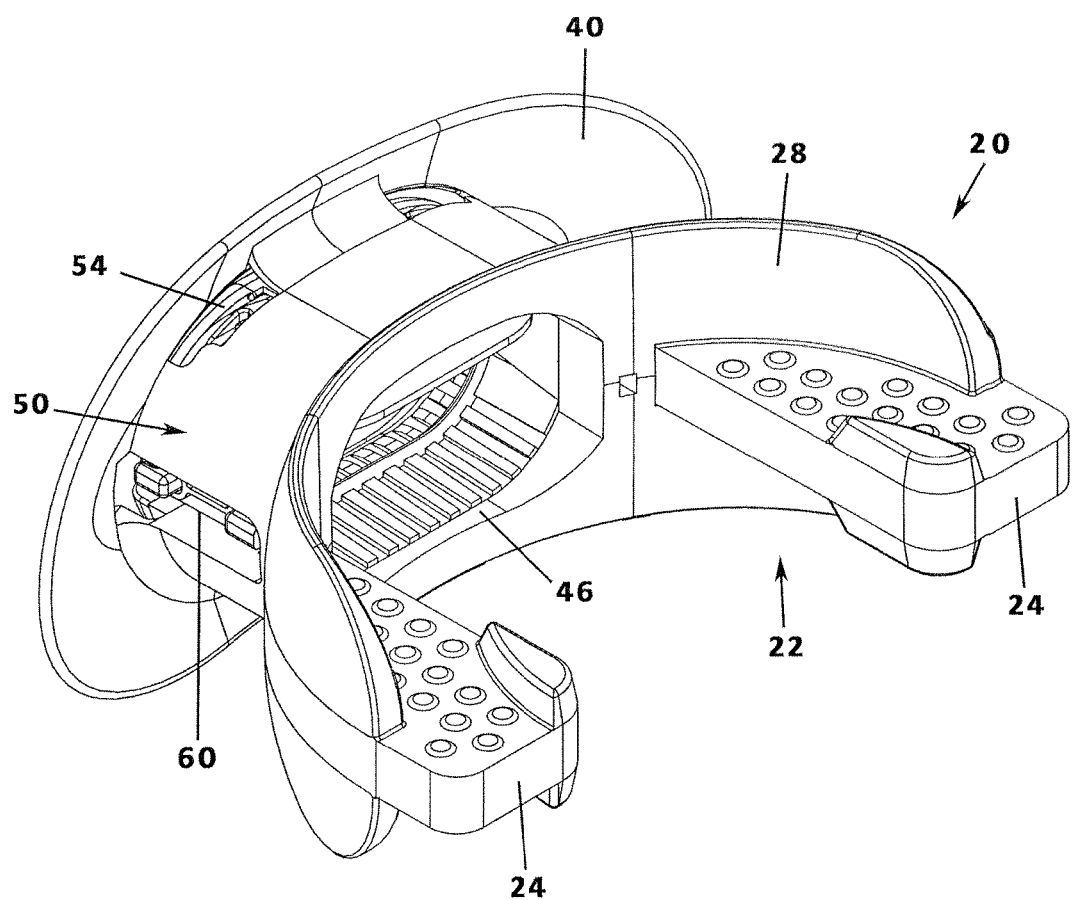
FIG. 20 is a rear perspective view of the bi-directional oxygenation apparatus of FIG. 19.
Figure 21:
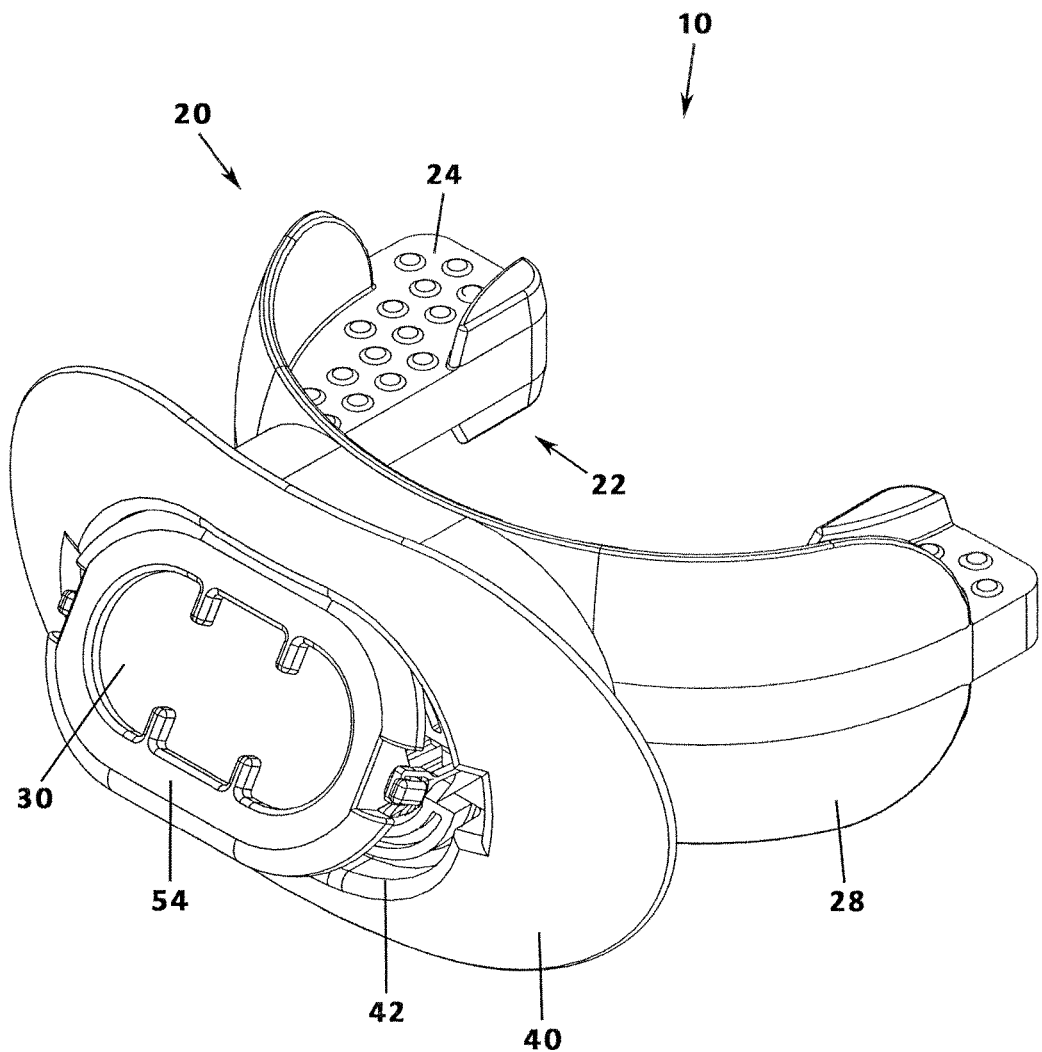
FIG. 21 is front perspective view of the bi-directional oxygenation apparatus of FIG. 19, illustrated with the end shield in an open or extended configuration.
Figure 22:
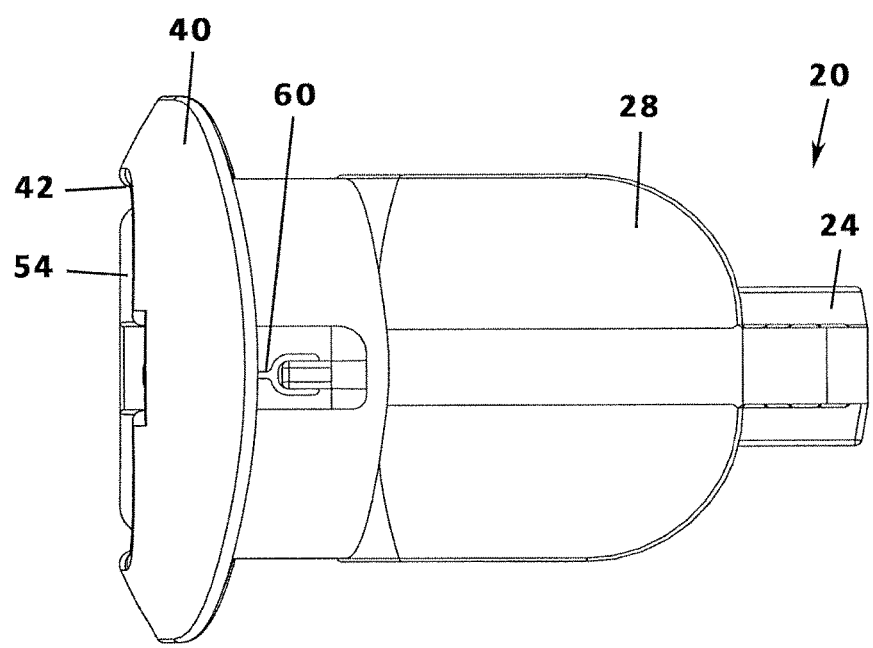
FIG. 22 is a side view of the bi-directional oxygenation apparatus of FIG. 19.
Figure 23:
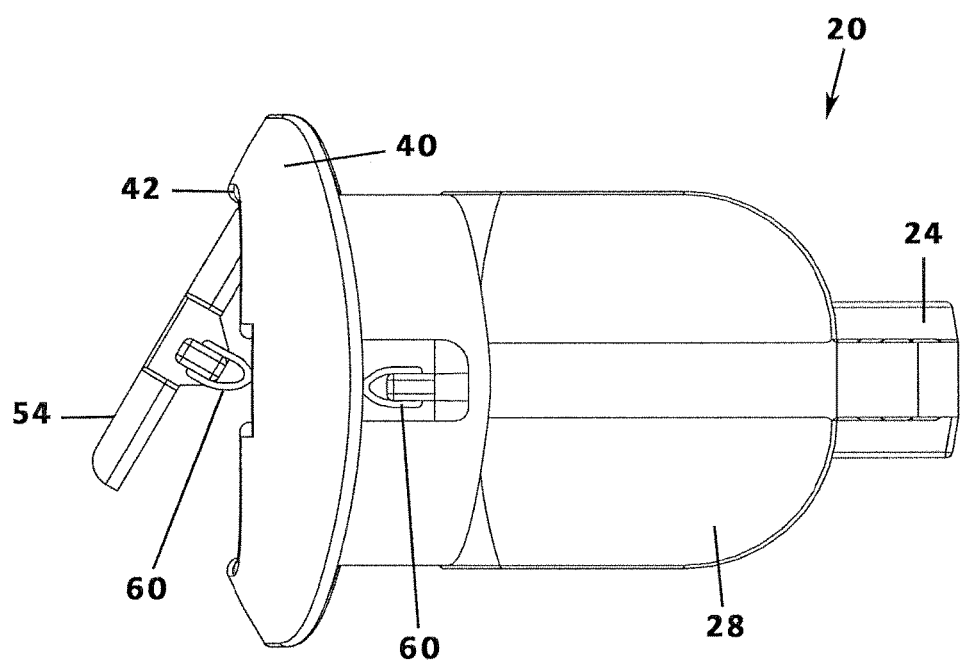
FIG. 23 is a side view of the bi-directional oxygenation apparatus of FIG. 21.

In another aspect, the bi-directional oxygenation apparatus 10 includes an external mouth shield 40 coupled to the distal end of the continuous side wall 52 of the vent member 50 (FIG. 19). It is understood that while the external mouth shield 40 has been removed from FIGS. 1-18, such removal is for clarity and not an indication of not being a part of a preferred embodiment. The external mouth shield 40 has a bowed or curved configuration toward the mouth shield 28 of the mouthpiece 20. The external mouth shield 40 is to be contrasted with the mouth shield 28 first described above and which may also be referred to as an internal mouth shield. More particularly, the internal mouth shield 28 has a configuration that conforms to the inner surface of a user's lips. By contrast, the external mouth shield 40 has a configuration that conforms to the exterior surface of a user's lips and cheeks. In an embodiment, the internal mouth shield 28 and external mouth shield 40 are concentric or even parallel to one another. The external mouth shield 40 defines a void 42 of a sufficient diameter or irregular dimension that allows the end shield 54 to extend and be accessible therethrough. In other words, inhaled and exhaled air is allowed to pass through the external mouth shield 40. Stated another way, the interior area of the vent member 50 and central orifice 27 defined by the mouthpiece 20 are accessible through the void 42 without any resistance or blockage.

In still another aspect, a lower or bottom interior surface of the external portion 26 may be recessed to define a collection area 46. More particularly, the collection area 46 is configured to collect saliva that may come through the central orifice 27 as part of the air exhaled by a patient. The collection area 46 may include a rearwardly and downwardly angled surface such that collected saliva is returned to the mouthpiece and, ultimately, to the mouth of the patient. This structure is important so that moisture is not accumulated on the surface of the restraining member 30. The bottom interior surface of the external portion 26 may include a plurality of grooves or recessed channels 53 that contribute to efficient collection of saliva and returning collected saliva to the patient's mouth as described above.

In use, a non-intubated patient or any user desiring to enhance the oxygenation of his blood by expansion of his lung capacity can inhale and exhale through the football style mouthpiece 20 of the bi-directional oxygenation apparatus 10 as described above. Ambient air may be inhaled without any resistance as inhalation causes the resistance member 30 to move between open and closed configurations as described above. Then, the inhaled air may be exhaled through the mouthpiece, the exhaled air causing the resistance member 30 to bear against the grill of the vent member 50 which provides mechanical resistance as exhaled air must pass through the openings 38. The resistance member 30 may cause the end shield 54 to push the end shield outwardly against the natural bias of the elastic members 60. With each cycle of inhalation and then exhalation, the lungs of the patient are expanded, more oxygen is retained at the conclusion of an exhalation and, as a result, more oxygen is received into the blood (i.e. oxygenation occurs). The external mouth shield 40 may protect the rearward components of the invention from damage caused by impact forces.

Accordingly, the present invention allows oxygenation enhancement therapy to be available to a non-intubated patient.

It is understood that while certain forms of this invention have been illustrated and described, it is not limited thereto except insofar as such limitations are included in the following claims and allowable functional equivalents thereof.

The invention claimed is:

1. A self-administered oxygenation apparatus for increasing pressure within a non-intubated patient's lungs and thereby expanding collapsed alveoli and thereby increasing an amount of oxygen in a patient's blood when operated singly by the non-intubated patient who is capable of unassisted inhalation and exhalation, said self-administered oxygenation apparatus comprising:
a mouthpiece having an external portion defining a center orifice through which the patient selectively inhales and exhales air;
a vent member having a continuous side wall coupled to said external portion of said mouthpiece and defining an interior area in fluid communication with said center orifice;
wherein said vent member includes an end shield operable to partially block access to the interior area while still allowing inhalation or exhalation of air therethrough, said end shield being movable toward or away from said vent member when air is inhaled or exhaled through said center orifice, respectively;
an elastic member having a loop of resilient material coupled to an external surface of said continuous side wall of said vent member in a tightening, biased relationship for operatively coupling said end shield to said vent member, said elastic member continuously biasing said end shield toward said vent member;
a resistance member coupled to said vent member and positioned between said interior area of said vent member and said mouthpiece, said resistance member being pivotally operable to allow ambient air inhaled by the patient to pass thereby without resistance and to decrease a flow of air exhaled by the patient;
wherein said resistance member is moved to an open configuration directed away from said end shield and toward said mouthpiece when air is inhaled for allowing movement of air toward said mouthpiece;
wherein said resistance member is moved to a closed configuration that bears against said end shield when air is exhaled for resisting movement of air toward said end shield.

2. The self-administered oxygenation apparatus as in claim 1, wherein said resistance member is a one-way positive-end expiratory pressure ("PEEP") valve operable to resist air exhaled by the patient through said center orifice.

3. The self-administered oxygenation apparatus as in claim 1, wherein said resistance member includes at least one opening through which air is allowed to pass when said resistance member is at said closed configuration and when air is exhaled.

4. The self-administered oxygenation apparatus as in claim 1, wherein said resistance member has a single panel having an upper edge coupled to said continuous side wall of said vent member and having a planar configuration.

5. The self-administered oxygenation apparatus as in claim 1, wherein said elastic member is a rubber band that selectively expands in length when said end shield is moved away from said vent member and is resilient to return to an original length when said end shield is moved toward said vent member.

6. The self-administered apparatus as in claim 1, wherein said resistance member is constructed of silicone.

7. The self-administered apparatus as in claim 1, wherein said mouthpiece includes an intraoral portion for placement in the patient's mouth, said intraoral portion being coupled to said external portion and in fluid communication with said center orifice.

8. The self-administered apparatus as in claim 7, wherein: said intraoral portion of said mouthpiece includes left and right grip members arranged in a bowed configuration and configured for insertion between the teeth of the patient; said mouthpiece includes a mouth shield intermediate said intraoral portion and said external portion, said mouth shield having a hemispherical shape configuration extending along said intraoral portion and configure to conform to an inner surface of the patient's lips.

9. The self-administered apparatus as in claim 8, further comprising an external mouth shield operably coupled to a distal end of the vent member and having a bowed shape configuration that conforms to an exterior surface of the patient's lips, said external mouth shield defining a void through which said end shield extends.

10. The self-administered apparatus as in claim 1, wherein an interior surface of said external portion of said mouthpiece defines a collection area that is configured to collect saliva that passes through said central orifice, said collection area having a downwardly angled surface in a direction toward said mouthpiece so as to return collected saliva thereto.

11. A self-administered oxygenation apparatus for increasing pressure within a non-intubated patient's lungs and thereby expanding collapsed alveoli and thereby increasing an amount of oxygen in a patient's blood when operated singly by the non-intubated patient who is capable of unassisted inhalation and exhalation, said self-administered oxygenation apparatus comprising:

a mouthpiece having an external portion defining a center orifice through which the patient selectively inhales and exhales air;

a vent member having a continuous side wall coupled to said external portion of said mouthpiece and defining an interior area in fluid communication with said center orifice;

wherein said vent member includes an end shield operable to partially block access to the interior area while still allowing inhalation or exhalation of air therethrough, said end shield being movable toward or away from said vent member when air is inhaled or exhaled through said center orifice, respectively;

an elastic member having a loop of resilient material coupled to an external surface of said continuous side wall of said vent member in a tightening, biased relationship for operatively coupling said end shield to said vent member, said elastic member continuously biasing said end shield toward said vent member;

a one-way positive-end expiratory pressure ("PEEP") valve coupled to said continuous side wall of said vent member and positioned between said interior area of said vent member and said mouthpiece, said PEEP valve being pivotally operable to allow ambient air inhaled by the patient to pass thereby without resistance and to decrease a flow of air exhaled by the patient so as to resist air exhaled by the patient;

wherein said PEEP valve is moved to an open configuration directed away from said end shield and toward said mouthpiece when air is inhaled for allowing movement of air toward said mouthpiece;

wherein said PEEP valve is moved to a closed configuration that bears against said end shield when air is exhaled for resisting movement of air toward said end shield.

12. The self-administered oxygenation apparatus as in claim 11, wherein said PEEP valve defines at least one opening through which air is allowed to pass when said resistance member is at said closed configuration and when air is exhaled.

13. The self-administered oxygenation apparatus as in claim 11, wherein said resistance member has a single panel having an upper edge coupled to said continuous side wall of said vent member and having a planar configuration.

14. The self-administered oxygenation apparatus as in claim 11, wherein said elastic member is a rubber band that selectively expands in length when said end shield is moved away from said vent member and is resilient to return to an original length when said end shield is moved toward said vent member.

15. The self-administered apparatus as in claim 11, wherein said PEEP valve is constructed of silicone.

16. The self-administered apparatus as in claim 11, wherein said mouthpiece includes an intraoral portion for placement in the patient's mouth, said intraoral portion being coupled to said external portion and in fluid communication with said center orifice.

17. The self-administered apparatus as in claim 16, wherein: said intraoral portion of said mouthpiece includes left and right grip members arranged in a bowed configuration and configured for insertion between the teeth of the patient; said mouthpiece includes a mouth shield intermediate said intraoral portion and said external portion, said mouth shield having a hemispherical shape configuration extending along said intraoral portion and configure to conform to an inner surface of the patient's lips.

18. The self-administered apparatus as in claim 17, further comprising an external mouth shield operably coupled to a distal end of the vent member and having a bowed shape configuration that conforms to an exterior surface of the patient's lips, said external mouth shield defining a void through which said end shield extends.

19. The self-administered apparatus as in claim 11, wherein an interior surface of said external portion of said mouthpiece defines a collection area that is configured to collect saliva that passes through said central orifice, said collection area having a downwardly angled surface in a direction toward said mouthpiece so as to return collected saliva thereto.

* * * * *